(12) United States Patent
Schmidt et al.

(10) Patent No.: US 7,462,367 B2
(45) Date of Patent: *Dec. 9, 2008

(54) ANTICHOLINERGIC POWDER FORMULATIONS FOR INHALATION

(75) Inventors: Friedrich Schmidt, Ingelheim (DE); Michael Trunk, Ingelheim (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 179 days.

This patent is subject to a terminal disclaimer.

(21) Appl. No.: 10/880,684

(22) Filed: Jun. 30, 2004

(65) Prior Publication Data

US 2005/0226818 A1 Oct. 13, 2005

Related U.S. Application Data

(60) Provisional application No. 60/508,028, filed on Oct. 2, 2003.

(30) Foreign Application Priority Data

Jul. 11, 2003 (DE) ................. 103 31 350

(51) Int. Cl.
A61K 31/46 (2006.01)
A61K 9/14 (2006.01)
A61K 9/48 (2006.01)

(52) U.S. Cl. .................. 424/489; 424/451; 514/291

(58) Field of Classification Search ........... 424/451, 424/489; 514/291
See application file for complete search history.

(56) References Cited

U.S. PATENT DOCUMENTS 6,706,726 B2 * 3/2004 Meissner et al. ............ 514/291

2004/0152720 A1 * 8/2004 Hartig et al. ................ 514/291

FOREIGN PATENT DOCUMENTS

WO   WO 02/30390   4/2002
WO   WO 02/32899   4/2002

\* cited by examiner

*Primary Examiner*—Johann Richter
*Assistant Examiner*—Konata M George
(74) *Attorney, Agent, or Firm*—Michael P. Morris; Mary Ellen M. Devlin; Wendy A. Petka

(57) ABSTRACT

An inhalable powder comprising:
(a) an active substance consisting essentially of a compound of formula 1

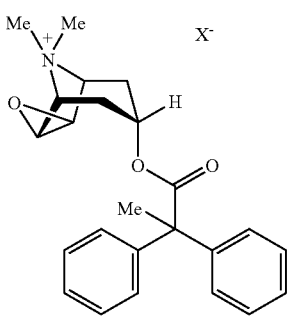

wherein $X^-$ is a pharmaceutically acceptable anion; and
(b) a physiologically acceptable excipient having an average particle size of 10 μm to 50 μm,
processes for preparing the inhalable powder, and methods of administration for the treatment of respiratory complaints, particularly for the treatment of chronic obstructive pulmonary disease (COPD) and asthma.

30 Claims, 1 Drawing Sheet

ANTICHOLINERGIC POWDER FORMULATIONS FOR INHALATION

RELATED APPLICATIONS

Figure 1:
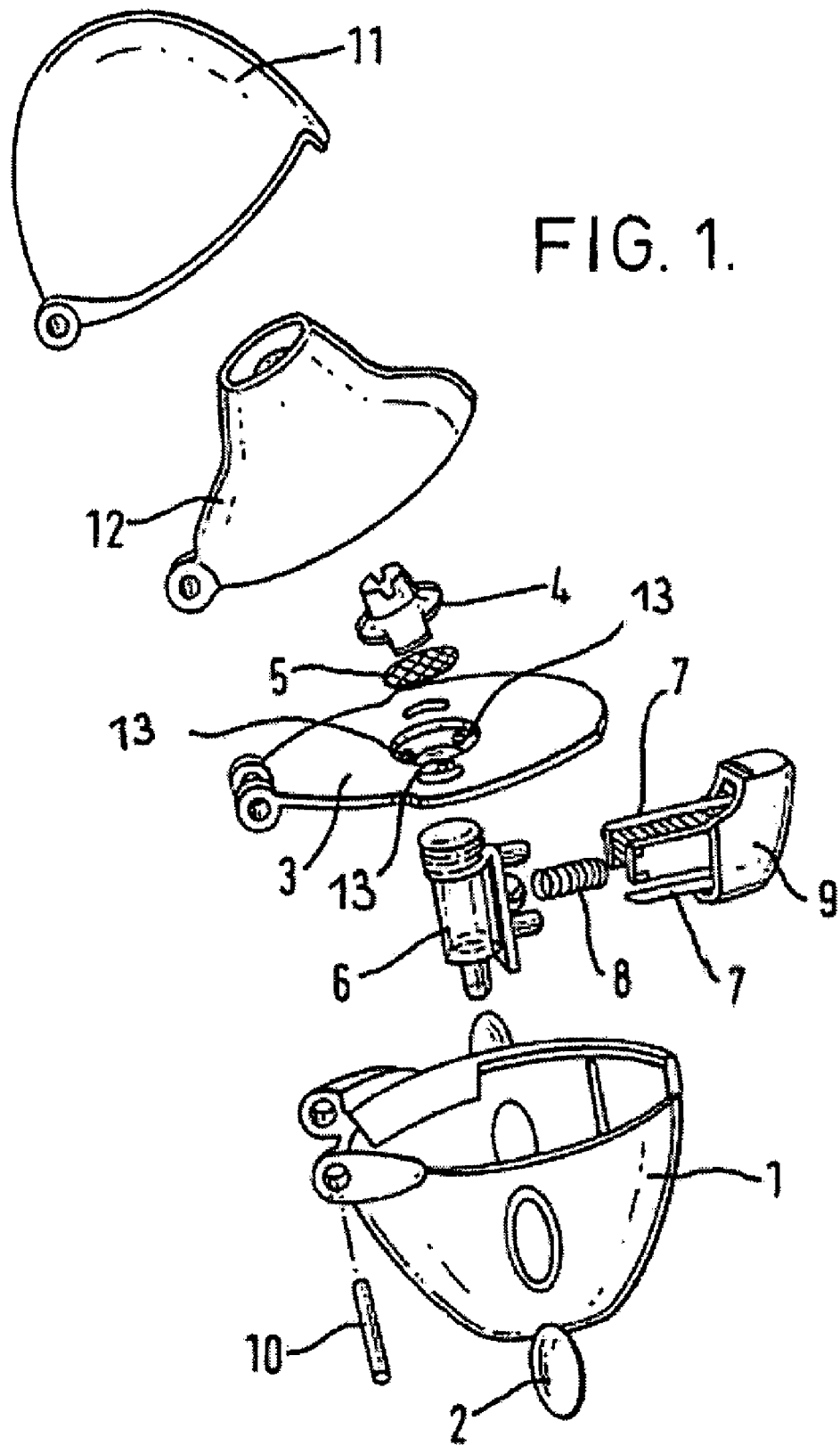

This application claims benefit of U.S. Ser. No. 60/508,028, filed Oct. 2, 2003, and claims priority to German Application No. 103 31 350.8, filed Jul. 11, 2003, each of which is hereby incorporated by reference in its entirety.

FIELD OF THE INVENTION

The invention relates to powder formulations for inhalation containing as the sole active substance an anticholinergic of formula 1

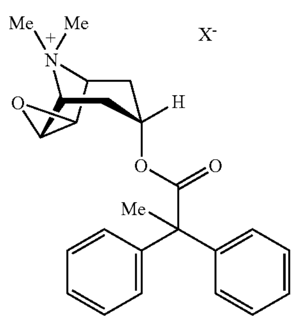

1 wherein $X^-$ may denote an anion having the meanings specified in the specification and in the claims, processes for preparing them, and their use for preparing a pharmaceutical composition for the treatment of respiratory complaints, particularly for the treatment of chronic obstructive pulmonary disease (COPD) and asthma.

BACKGROUND OF THE INVENTION

The compounds of formula 1 are known from WO 02/32899 (corresponding to U.S. Patent Application Pub. No. 2004/0087617, which is hereby incorporated by reference). They have valuable pharmacological properties and can provide therapeutic benefit as highly effective anticholinergics in the treatment of respiratory complaints, particularly in the treatment of inflammatory and/or obstructive diseases of the respiratory tract, particularly for treating asthma or chronic obstructive pulmonary disease (COPD).

When treating the above diseases, it is convenient to administer the active substance by inhalation. In addition to the administration by inhalation of broncholytically active compounds in the form of metered aerosols and inhalable solutions, the administration of inhalable powders containing active substance is also of particular importance.

In the case of active substances with a particularly high efficacy, only small amounts of the active substance are needed per single dose to achieve the therapeutically desired effect. In such cases, the active substance has to be diluted with suitable excipients to prepare the inhalable powder. Because of the large amount of excipient, the properties of the inhalable powder are critically influenced by the choice of excipient. When choosing the excipient, its particle size is particularly important. As a rule, the finer the excipient, the poorer its flow properties. However, good flow properties are a prerequisite for highly accurate metering when packing and dividing up the individual doses of preparation, e.g., when producing capsules (inhalettes) for powder inhalation or when the patient is metering the individual dose before using a multidose inhaler. Moreover, the particle size of the excipient is very important for the emptying characteristics of capsules when used in an inhaler. It has also been found that the particle size of the excipient has a considerable influence on the proportion of active substance in the inhalable powder which is delivered for inhalation. The term inhalable proportion of active substance refers to the particles of the inhalable powder which are conveyed deep into the branches of the lungs when inhaled with a breath. The particle size required for this is between 1 μm and 10 μm, preferably less than 6 μm.

The aim of the invention is to prepare an inhalable powder containing the active substance of formula 1 which, while being accurately metered (in terms of the quantity of active substance released and delivered to the lungs on each inhalation process) with only slight variations between batches, enables the active substance to be administered in a large inhalable proportion. A further aim of the present invention is to prepare an inhalable powder containing the active substance of formula 1 which ensures good emptying characteristics of the capsules, if the powder is administered by means of powder-filled capsules.

A further aim of the invention is to provide an inhalable powder which is characterized by a high degree of homogeneity of the powder mixture and minimal fluctuations in the dispersion characteristics from one batch of powder to the next. The homogeneity of the powder mixture and minor fluctuations in the dispersion properties are crucial in ensuring that the inhalable proportion of active substance is released reproducibly in constant amounts and hence with the lowest possible variability. Accordingly, the present invention also sets out to prepare an inhalable powder which allows the inhalable proportion of active substance to be administered with the lowest possible variability.

The characteristics of emptying from the powder reservoir (the container from which the inhalable powder containing the active substance is released for inhalation) play an important part, not exclusively, but especially in the administration of inhalable powders using powder-filled capsules. If only a small amount of the powder formulation is released from the powder reservoir as a result of minimal or poor emptying characteristics, significant amounts of the inhalable powder containing the active substance are left in the powder reservoir (e.g., the capsule) and are unavailable to the patient for therapeutic use. The result of this is that the dosage of active substance in the powder mixture has to be increased so that the quantity of active substance delivered is sufficient to produce the desired therapeutic effect.

Against this background, the present invention further sets out to provide an inhalable powder which is also characterized by very good emptying characteristics.

DESCRIPTION OF THE FIGURE

FIG. 1 shows an inhaler that may be used for administering the pharmaceutical composition of the invention in inhalettes.

DETAILED DESCRIPTION OF THE INVENTION

It was found that, surprisingly, the objectives outlined above can be achieved by means of the powdered preparations for inhalation (inhalable powders) according to the invention described hereinafter.

Accordingly, the present invention relates to inhalable powders containing as sole active substance a compound of formula 1

$$1$$

wherein X⁻ denotes a pharmaceutically acceptable anion, mixed with a physiologically acceptable excipient, characterized in that the excipient has an average particle size of 10 μm to 50 μm.

By the average particle size is meant here the 50% value of the volume distribution measured using a laser diffractometer by the dry dispersion method.

Preferred inhalable powders are those which contain as their sole active ingredient a compound of formula 1 wherein the anion X⁻ is selected from the group consisting of chloride, bromide, iodide, sulfate, phosphate, methanesulfonate, nitrate, maleate, acetate, citrate, fumarate, tartrate, oxalate, succinate, benzoate, and p-toluenesulfonate.

Preferably salts of formula 1 are used wherein X⁻ denotes an anion selected from among chloride, bromide, 4-toluenesulfonate, and methanesulfonate.

Particularly preferred within the scope of the present invention are those formulations which contain the compound of formula 1 wherein X⁻ denotes bromide as their sole active substance.

References to the compound of formula 1 within the scope of the present invention always include all possible amorphous and crystalline modifications of this compound. References to the compound of formula 1 within the scope of the present invention also include all possible solvates and hydrates which may be formed by this compound.

Any reference to the compound 1' within the scope of the present invention is to be regarded as a reference to the pharmacologically active cation of the formula shown below contained in the salts 1

$$1'$$

The content of active substance in the inhalable powders according to the invention is in the range from 0.0008% to 33%, based on the pharmacologically active cation 1'. Within the scope of the present invention, amounts given in percent are always to be interpreted as percent by weight unless specifically stated to the contrary.

Inhalable powders which contain 0.008% to 20.6% 1' are preferred according to the invention. Particularly preferred inhalable powders contain 1' in an amount of about 0.025% to 9.9%, preferably 0.05% to 6.6%, particularly preferably 0.07% to 3.3%. Lastly, inhalable powders which contain about 0.08% to 2.5% of cation 1' are of particular importance according to the invention.

The content of the compounds of formula 1 (cation 1' plus anion X⁻) can easily be calculated from the content of pharmacologically active cation 1' depending on the choice of the corresponding anion X⁻. If, for example, X⁻ denotes the bromide anion which is particularly preferred according to the invention, the inhalable powders according to the invention may contain between 0.001% and 40%, preferably 0.01% to 25% of compound 1 (in form of the bromide). Of particular interest according to the invention are inhalable powders which contain about 0.03% to 12%, preferably 0.06% to 8%, particularly preferably 0.08% to 4% of compound 1 in the form of the bromide. Of particular importance according to the invention are inhalable powders which contain about 0.1% to 3% of the compound of formula 1 (in the form of the bromide).

The formulations according to the invention contain the compounds of formula 1 as sole active substance. Pharmaceutical formulations which contain other active substances in addition to a compound of formula 1 are not the subject of this invention.

In particularly preferred inhalable powders, the excipient is characterized by an average particle size of 12 μm to 35 μm, particularly preferably from 13 μm to 30 μm.

Particularly preferred embodiments of the invention are further characterized in that the excipient has a 10% fine content of from 0.5 μm to 6 μm. The 10% fine content in this instance refers to the 10% value of the volume distribution measured using a laser diffractometer by the dry dispersion method.

Particularly preferred according to the invention are those inhalable powders wherein the 10% fine content is about 1 μm to 4 μm, preferably about 1.5 μm to 3 μm.

Also particularly preferred are those inhalable powders wherein the excipient has a specific surface area of 0.1 m²/g to 2 m²/g. By specific surface area is meant, for the purposes of the invention, the mass-specific powder surface area, calculated from the $N_2$ absorption isotherm which is observed at the boiling point of liquid nitrogen (method of Brunauer, Emmett, and Teller). Also preferred according to the invention are those inhalable powders wherein the excipient has a specific surface area of between 0.2 m²/g and 1.5 m²/g, preferably between 0.3 m²/g and 1.0 m²/g.

The excipients used for the purposes of the present invention are preferably prepared by suitable grinding and/or screening by common methods known in the art. The excipients used according to the invention may possibly also be mixtures of excipients obtained by mixing together excipient fractions of different mean particle sizes.

Examples of physiologically acceptable excipients which may be used to prepare the inhalable powders used for the inhalettes according to the invention include, for example, monosaccharides (e.g., glucose, fructose, or arabinose), disaccharides (e.g., lactose, saccharose, maltose, or trehalose), oligo- and polysaccharides (e.g., dextrans, dextrins, maltodextrin, starch, or cellulose), polyalcohols (e.g., sorbitol, mannitol, or xylitol), cyclodextrins (e.g., α-cyclodextrin, β-cyclodextrin, χ-cyclodextrin, methyl-β-cyclodextrin, or hydroxypropyl-β-cyclodextrin), amino acids (e.g., arginine hydrochloride) or salts (e.g., sodium chloride or calcium carbonate). Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Preferably, excipients of high crystallinity are used for the powder formulations according to the invention. This crystallinity can be assessed by means of the enthalpy released as the excipient is dissolved (solution enthalpy). In the case of the excipient lactose monohydrate, which is most preferably used according to the invention, it is preferable to use lactose which is characterized by a solution enthalpy of $\geq 45$ J/g, preferably $\geq 50$ J/g, particularly preferably $\geq 52$ J/g.

The inhalable powders according to the invention are characterized, in accordance with the problem on which the invention is based, by a high degree of homogeneity in the sense of the accuracy of single doses. This is in the region of <8%, preferably <6%, most preferably <4%.

After the starting materials have been weighed in, the inhalable powders are prepared from the excipient and the active substance using methods known in the art. Reference may be made to the disclosure of WO 02/30390 (corresponding to U.S. Pat. No. 6,585,959, which is hereby incorporated by reference), for example. The inhalable powders according to the invention may accordingly be obtained by the method described below, for example. In the preparation methods described hereinafter, the components are used in the proportions by weight described in the abovementioned compositions of the inhalable powders.

First, the excipient and the active substance are placed in a suitable mixing container. The active substance used has an average particle size of 0.5 μm to 10 μm, preferably 1 μm to 6 μm, most preferably 2 μm to 5 μm. The excipient and the active substance are preferably added using a sieve or a granulating sieve with a mesh size of 0.1 mm to 2 mm, preferably 0.3 mm to 1 mm, most preferably 0.3 mm to 0.6 mm. Preferably, the excipient is put in first and then the active substance is added to the mixing container. During this mixing process, the two components are preferably added in batches. It is particularly preferred to sieve in the two components in alternate layers. The mixing of the excipient with the active substance may take place while the two components are still being added. Preferably, however, mixing is only done once the two components have been sieved in layer by layer.

If after being chemically prepared the active substance used in the process described above is not already obtainable in a crystalline form with the particle sizes mentioned earlier, it can be ground up into the particle sizes which conform to the abovementioned parameters (so-called micronizing).

The micronizing process may be carried out using conventional mills. Preferably, the micronization is carried out with the exclusion of moisture, more preferably, using a corresponding inert gas such as nitrogen, for example. It has proved particularly preferable to use air jet mills in which the material is comminuted by the impact of the particles on one another and on the walls of the grinding container. According to the invention, nitrogen is preferably used as the grinding gas. The material for grinding is conveyed by the grinding gas under specific pressures (grinding pressure). Within the scope of the present invention, the grinding pressure is usually set to a value between about 2 bar and 8 bar, preferably between about 3 bar and 7 bar, most preferably between about 3.5 bar and 6.5 bar. The material for grinding is fed into the air jet mill by means of the feed gas under specific pressures (feed pressure). Within the scope of the present invention a feed pressure of between about 2 bar and 8 bar, preferably between about 3 bar and 7 bar, and most preferably between about 3.5 bar and 6 bar, has proved satisfactory. The feed gas used is also preferably an inert gas, most preferably nitrogen again. The material to be ground (crystalline compound of formula 1) may be fed in at a rate of about 5 g/min to 35 g/min, preferably at about 10 g/min to 30 g/min.

For example, without restricting the subject of the invention thereto, the following apparatus has proved suitable as a possible embodiment of an air jet mill: a 2-inch Micronizer with grinding ring, 0.8 mm bore, made by Messrs. Sturtevant Inc., 348 Circuit Street, Hanover, Mass. 02239, USA. Using this apparatus, the grinding process is preferably carried out with the following grinding parameters: grinding pressure: about 4.5 bar to 6.5 bar; feed pressure: about 4.5 bar to 6.5 bar; and supply of grinding material: about 17 g/min to 21 g/min.

It may optionally be advantageous to add a finer excipient fraction with an average particle size of 1 μm to 9 μm to the inhalable powders according to the invention. Such inhalable powders which contain in addition to the active substance of formula 1 an excipient mixture which comprises, in addition to the excipient with an average particle size of 10 μm to 50 μm mentioned hereinbefore, a specifically added excipient fraction with an average particle size of 1 μm to 9 μm, are preferably prepared by first mixing the two excipient fractions and then adding the active substance to this excipient mixture. Suitable processes for preparing active substance formulations of this kind are known in the art (e.g., WO 02/30390, WO 03/017970, and WO 03/017979 (corresponding to U.S. Pat. No. 6,585,959 and U.S. Patent Application Pub. Nos. 2003/0043687 and 2003/0068278, respectively, each which is hereby incorporated by reference)).

If excipient mixtures of coarser and finer excipient fractions are used, the proportion of finer excipient in the total quantity of excipient is preferably 1% to 20%.

If excipient mixtures of coarser and finer excipient fractions are used, the coarser excipient fraction preferably has the abovementioned properties in terms of mean particle size, specific surface area or crystallinity, whereas the finer excipient fraction mixed therewith is preferably characterized by an average particle size of from 2 μm to 8 μm, particularly preferably from 3 μm to 7 μm. Furthermore, the proportion of fine excipient fraction in the total quantity of excipient in inhalable powders of this kind which may be used is preferably 3% to 15%, particularly preferably 5% to 10%.

The present invention also relates to the use of the inhalable powders according to the invention for preparing a pharmaceutical composition for the treatment of respiratory complaints, particularly for the treatment of COPD and/or asthma.

The inhalable powders according to the invention may, for example, be administered by means of inhalers which deliver a single dose from a supply using a measuring chamber as described in U.S. Pat. No. 4,570,630, which is hereby incorporated by reference, or by other means as described in DE 36 25 685 A.

Alternatively and of equivalent significance according to the invention, the inhalable powders according to the invention may also be administered using inhalers which contain the inhalable powder in a number of individually packaged doses (Pre-Metered Dry Powder Inhaler).

Alternatively and of equivalent significance according to the invention, the inhalable powders according to the invention may also be packaged in capsules which are administered in inhalers such as those described in WO 94/28958 (corresponding to U.S. Pat. No. 5,947,118, which is hereby incorporated by reference), for example. The inhaler described in WO 94/28958 and U.S. Pat. No. 5,947,118 is hereinafter referred to as the "Hochrainer-Kinnear inhaler".

Particularly preferably, the capsules containing the inhalable powder according to the invention are administered using an inhaler as shown in FIG. 1. This inhaler is characterized by a housing 1 containing two windows 2, a deck 3 in which there are air inlet ports and which is provided with a screen 5 secured via a screen housing 4, an inhalation chamber 6 connected to the deck 3 on which there is a push button 9 provided with two sharpened pins 7 and movable counter to a spring 8, and a mouthpiece 12 which is connected to the housing 1, the deck 3 and a cover 11 via a spindle 10 to enable it to be flipped open or shut, as well as air through-holes 13 for adjusting the flow resistance.

The present invention further relates to the use of the inhalable powders according to the invention for preparing a pharmaceutical composition for the treatment of respiratory complaints, particularly for the treatment of COPD and/or asthma, characterized in that the inhaler described above and shown in FIG. 1 is used.

Capsules made of all kinds of materials may be used for administering the inhalable powders according to the invention by means of powder-filled capsules. By capsule material is meant, within the scope of the present invention, the material from which the shell of the capsule for inhalation is made. The capsule material is preferably selected according to the invention from among gelatine, cellulose derivatives, starch, starch derivatives, chitosan, and synthetic plastics.

If gelatine is used as the capsule material, it may be used in admixture with other additives selected from among polyethyleneglycol (PEG), preferably PEG 3350, glycerol, sorbitol, propyleneglycol, PEO-PPO block copolymers, and other polyalcohols and polyethers. Within the scope of the present invention gelatine is used particularly preferably in admixture with PEG, preferably PEG 3350. A gelatine capsule according to the invention preferably contains PEG in an amount of 1% to 10% (wt.-%), preferably 3% to 8%. Particularly preferred gelatine capsules contain PEG in an amount of 4% to 6%, a PEG content of about 5% being most preferred according to the invention.

If cellulose derivatives are used as the capsule material, it is preferable to use hydroxypropylmethylcellulose, hydroxypropylcellulose, methylcellulose, hydroxymethylcellulose, and hydroxyethylcellulose. In this case, hydroxypropylmethylcellulose (HPMC), particularly preferably HPMC 2910, is used as the capsule material.

If synthetic plastics are used as the capsule material, these are preferably selected according to the invention from among polyethylene, polycarbonate, polyester, polypropylene, and polyethylene terephthalate. Particularly preferred synthetic plastics are polyethylene, polycarbonate, or polyethylene terephthalate. If polyethylene is used as one of the particularly preferred capsule materials according to the invention, polyethylene with a density of between 900 kg/m$^3$ and 1000 kg/m$^3$, preferably from 940 kg/m$^3$ to 980 kg/m$^3$, particularly preferably 960 kg/m$^3$ to 970 kg/m$^3$ is preferably used (high-density polyethylene).

The synthetic plastics according to the invention may be processed in various ways using manufacturing methods known in the art. Processing of the plastics by injection molding is preferred according to the invention. Injection molding without the use of mold release agents is particularly preferred. This manufacturing method is well-defined and is characterized by particularly good reproducibility.

In another aspect the present invention relates to the abovementioned capsules containing the inhalable powder according to the invention as mentioned hereinbefore. These capsules may contain approximately 1 mg to 20 mg, preferably about 3 mg to 15 mg, particularly preferably about 4 mg to 6 mg of inhalable powder.

The present invention also relates to an inhalation kit consisting of one or more of the above capsules characterized in that it contains inhalable powder according to the invention in conjunction with the inhaler according to FIG. 1.

The present invention also relates to the use of the abovementioned capsules characterized by their content of inhalable powder according to the invention, for preparing a pharmaceutical composition for the treatment of respiratory complaints, particularly for the treatment of COPD and/or asthma.

Filled capsules containing the inhalable powders according to the invention are produced by methods known in the art by filling the empty capsules with the inhalable powders according to the invention.

The following Examples serve to illustrate the present invention still further without restricting the scope of the invention to the following embodiments described by way of example.

Starting Materials

I. Excipient

In the Examples that follow lactose monohydrate is used as excipient. It may be obtained for example from Borculo Domo Ingredients, Borculo, NL, under the product name Lactochem Extra Fine Powder. The specifications according to the invention for the particle size and specific surface area are met by this grade of lactose. In addition, this lactose has the abovementioned preferred solution enthalpy values for lactose according to the invention.

II. Micronization of the Compound of Formula 1 (Where X$^-$ is Bromide)

The crystalline 2,2-diphenylpropionic acid scopine ester methobromide which may be obtained according to WO 02/32899 (the compound of formula 1 where X$^-$ is bromide) is micronized with an air jet mill of the 2-inch micronizer-type with grinding ring, 0.8 mm bore, made by Messrs Sturtevant Inc., 348 Circuit Street, Hanover, Mass. 02239, USA.

Using nitrogen as the grinding gas, the following grinding parameters are set, for example: grinding pressure: 5.5 bar; feed pressure: 5.5 bar; and feed: 19 g/min.

Measuring Methods

I. Determining the Particle Size of the Micronized Compound of Formula 1 (Where X$^-$ is Bromide)

Measuring Equipment and Settings

The equipment is operated according to the manufacturer's instructions.

| | |
|---|---|
| Measuring equipment: | Laser-diffraction spectrometer (HELOS), SympaTec |
| Dispersing unit: | RODOS dry disperser with suction funnel, SympaTec |
| Sample quantity: | 200 mg ± 150 mg |
| Product feed: | Vibri Vibrating channel, Messrs. Sympatec |
| Frequency of vibrating channel: | rising to 100% |
| Duration of sample feed: | 15 to 25 sec. (in the case of 200 mg) |
| Focal length: | 100 mm (measuring range: 0.9-175 μm) |
| Measuring/waiting time: | about 15 s (in the case of 200 mg) |
| Cycle time: | 20 ms |
| Start/stop at: | 1% on channel 28 |
| Dispersing gas: | compressed air |

| | |
|---|---|
| Pressure: | 3 bar |
| Vacuum: | maximum |
| Evaluation method: | HRLD |

Sample Preparation/Product Feed

About 200 mg of the test substance is weighed onto a piece of card. Using another piece of card, all the larger lumps are broken up. The powder is then sprinkled finely over the front half of the vibrating channel (starting about 1 cm from the front edge). After the start of the measurement, the frequency of the vibrating channel is varied so that the sample is fed in as continuously as possible. However, the quantity of product should not be too great either, so as to ensure adequate dispersal.

II. Determining the Particle Size of the Lactose

Measuring Equipment and Settings

The equipment is operated according to the manufacturer's instructions.

| | |
|---|---|
| Measuring equipment: | Laser-diffraction spectrometer (HELOS), SympaTec |
| Dispersing unit: | RODOS dry disperser with suction funnel, SympaTec |
| Sample quantity: | 200 mg ± 100 mg |
| Product feed: | Vibri Vibrating channel, Messrs. Sympatec |
| Frequency of vibrating channel: | 100% rising |
| Focal length: | 200 mm (measuring range: 1.8-350 μm) |
| Measuring/waiting time: | about 10 s (in the case of 200 mg) |
| Cycle time: | 10 ms |
| Start/stop at: | 1% on channel 28 |
| Dispersing gas: | compressed air |
| Pressure: | 3 bar |
| Vacuum: | maximum |
| Evaluation method: | HRLD |

Sample Preparation/Product Feed

About 200 mg of the test substance is weighed onto a piece of card. Using another piece of card, all the larger lumps are broken up. The powder is transferred into the vibrating channel. A gap of 1.2 to 1.4 mm is set between the vibrating channel and funnel. After the start of the measurement, the frequency of the vibrating channel is increased as continuously as possible to 100% towards the end of the measurement.

III. Determining the Specific Surface Area of the Lactose (Multipoint BET Method)

Method

The specific surface is determined by exposing the powder sample to a nitrogen atmosphere at different pressures. Cooling the sample causes the nitrogen molecules to be condensed on the surface of the particles. The quantity of condensed nitrogen is determined by means of the drop in pressure in the system and the specific surface of the sample is calculated by means of the surface nitrogen requirement and the weight of the sample.

The equipment is operated according to the manufacturer's instructions.

Measuring Equipment and Settings

| | |
|---|---|
| Measuring equipment: | Tri Star Multi Point BET, Messrs Micromeritics |
| Heater: | VacPrep 061, Messrs. Micromeritics |
| Heating: | about 12 hours/40° C. |
| Sample tube: | ½ inch; use filler rod |
| Analysis Condition: | 10 point BET surface 0.1 to 0.20 p/p0 |
| Absolute P. tolerance: | 5.0 mmHg |
| rel. P. tolerance: | 5.0% |
| Evacuation rate: | 50.0 mmHg/sec. |
| Unrestricted evac f.: | 10.0 mmHg |
| Evac. time: | 0.1 hours |
| Free Space: | Lower Dewar, time: 0.5 h |
| Equilibration interv. | 20 sec |
| Min. equl. delay: | 600 sec |
| Adsorptive: | Nitrogen |

IV. Determining the Heat of Solution (Enthalpy of Solution) $E_c$

The solution enthalpy is determined using a solution calorimeter 2225 Precision Solution Calorimeter made by Messrs. Thermometric. The heat of solution is calculated by means of the change in temperature occurring (as a result of the dissolving process) and the system-related change in temperature calculated from the base line. Before and after the ampoule is broken, electrical calibration is carried out with an integrated heating resistor of a precisely known power. A known heat output is delivered to the system over a set period and the jump in temperature is determined.

Method and Equipment Parameters

| | |
|---|---|
| Solution calorimeter: | 2225 Precision Solution Calorimeter, Messrs. Thermometric |
| Reaction cell: | 100 mL |
| Thermistor resistance: | 30.0 kΩ (at 25° C.) |
| Speed of stirrer: | 500 U/min |
| Thermostat: | Thermostat of 2277 Thermal Activity Monitor TAM, Messrs. Thermometric |
| Temperature: | 25° C. ± 0.0001° C. (over 24 hours) |
| Measuring ampoules: | Crushing ampoules 1 mL, Messrs. Thermometric |
| Seal: | Silicon stopper and beeswax, Messrs. Thermometric |
| Weight: | 40 mg to 50 mg |
| Solvent: | Chemically pure water |
| Volume of solvent: | 100 mL |
| Bath temperature: | 25° C. |
| Temperature resolution: | High |
| Starting temperature: | −40 mK (±10 mK) temperature-offset |
| Interface: | 2280-002 TAM accessory interface 50 Hz, Messrs. Thermometric |
| Software: | SolCal V 1.1 for WINDOWS |
| Evaluation: | Automatic evaluation with Menu point CALCULATION/ANALYSE EXPERIMENT (Dynamics of base line; calibration after breakage of ampoule). |

Electrical Calibration

The electrical calibration takes place during the measurement, once before and once after the breakage of the ampoule. The calibration after the breakage of the ampoule is used for the evaluation.

| | |
|---|---|
| Amount of heat: | 2.5 J |
| Heating power: | 500 mW |
| Heating time: | 10 sec. |
| Duration of base lines: | 5 minutes (before and after heating) |

Preparation of the Powder Formulations According to the Invention

I. Apparatus

The following machines and equipment, for example, may be used to prepare the inhalable powders:

Mixing container or powder mixer: Turbulamischer 2 L, Type 2C; made by Willy A. Bachofen AG, CH-4500 Basel.

Hand-held screen: 0.135 mm mesh size

The empty inhalation capsules may be filled with inhalable powders containing the active substance by hand or mechanically. The following equipment may be used.

Capsule filling machine: MG2, Type G100, manufacturer: MG2 S.r.l, I-40065 Pian di Macina di Pianoro (BO), Italy

EXAMPLE 1

Powder Mixture

To prepare the powder mixture, 297.0 g of excipient and 3.0 g of micronized compound of formula 1 (wherein $X^-$ is bromide) are used. In the resulting 300 g of inhalable powder, the content of active substance is 1% (based on compound of formula 1 wherein $X^-$ is bromide). In terms of the pharmacologically active cation 1', this active substance content corresponds to a proportion of about 0.825%.

About 40 g to 45 g of excipient are placed in a suitable mixing container through a hand-held screen with a mesh size of 0.315 mm. Then micronized compound of formula 1 (wherein $X^-$ is bromide) in batches of about 450 mg to 550 mg and excipient in batches of about 40 g to 45 g are screened in by alternate layers. The excipient and active substance are added in 7 and 6 layers, respectively.

Having been screened in, the ingredients are then mixed (mixing speed 900 rpm). The final mixture is passed twice more through a hand-held screen and then mixed again at 900 rpm.

Using the method described in Example 1 or analogously thereto, the following powders for inhalation may be obtained, for example:

EXAMPLE 2

| | |
|---|---|
| active substance 1 ($X^-$ is bromide) | 3.000 g |
| lactose monohydrate* | 297.000 g |
| Total | 300.000 g |

*the excipient is characterized by the following parameters: average particle size: 17.9 μm; 10% fine content: 2.3 μm; and specific surface area: 0.61 m$^2$/g.

EXAMPLE 3

| | |
|---|---|
| active substance 1 ($X^-$ is bromide) | 3.000 g |
| lactose monohydrate* | 297.000 g |
| Total | 300.000 g |

*the excipient is characterized by the following parameters: average particle size: 18.5 μm; 10% fine content: 2.2 μm; and specific surface area: 0.83 m$^2$/g.

EXAMPLE 4

| | |
|---|---|
| active substance 1 ($X^-$ is bromide) | 3.000 g |
| lactose monohydrate* | 297.000 g |
| Total | 300.000 g |

*the excipient is characterized by the following parameters: average particle size: 21.6 μm; 10% fine content: 2.5 μm; and specific surface area: 0.59 m$^2$/g.

EXAMPLE 5

| | |
|---|---|
| active substance 1 ($X^-$ is bromide) | 3.000 g |
| lactose monohydrate* | 297.000 g |
| Total | 300.000 g |

*the excipient is characterized by the following parameters: average particle size: 16.0 μm; 10% fine content: 2.0 μm; and specific surface area: 0.79 m$^2$/g;

EXAMPLE 6

| | |
|---|---|
| active substance 1 ($X^-$ is bromide) | 6.000 g |
| lactose monohydrate* | 294.000 g |
| Total | 300.000 g |

*the excipient is characterized by the following parameters: average particle size: 17.9 μm; 10% fine content: 2.3 μm; and specific surface area: 0.61 m$^2$/g.

EXAMPLE 7

| | |
|---|---|
| active substance 1 ($X^-$ is bromide) | 6.000 g |
| lactose monohydrate* | 294.000 g |
| Total | 300.000 g |

*the excipient is characterized by the following parameters: average particle size: 18.5 μm; 10% fine content: 2.2 μm; and specific surface area: 0.83 m$^2$/g.

EXAMPLE 8

| | |
|---|---|
| active substance 1 ($X^-$ is bromide) | 1.500 g |
| lactose monohydrate* | 298.500 g |
| Total | 300.000 g |

*the excipient is characterized by the following parameters: average particle size: 17.9 μm; 10% fine content: 2.3 μm; and specific surface area: 0.61 m$^2$/g.

EXAMPLE 9

| | |
|---|---|
| active substance 1 ($X^-$ is bromide) | 1.500 g |
| lactose monohydrate* | 298.500 g |
| Total | 300.000 g |

*the excipient is characterized by the following parameters: average particle size: 18.5 μm; 10% fine content: 2.2 μm; and specific surface area: 0.83 $m^2/g$.

EXAMPLE 10

| | |
|---|---|
| active substance 1 ($X^-$ is bromide) | 6.000 g |
| dextrose monohydrate* | 294.000 g |
| Total | 300.000 g |

*the excipient is characterized by the following parameters: average particle size: 18.5 μm; and 10% fine content: 2.2 μm.

EXAMPLE 11

| | |
|---|---|
| active substance 1 ($X^-$ is bromide) | 1.500 g |
| dextrose monohydrate* | 298.500 g |
| Total | 300.000 g |

*the excipient is characterized by the following parameters: average particle size: 17.9 μm; and 10% fine content: 2.3 μm.

EXAMPLE 12

| | |
|---|---|
| active substance 1 ($X^-$ is bromide) | 3.000 g |
| dextrose monohydrate* | 297.000 g |
| Total | 300.000 g |

*the excipient is characterized by the following parameters: average particle size: 18.5 μm; and 10% fine content: 2.2 μm.

The formulations in the above Examples may be packed in appropriate amounts into suitable packaging means, e.g., polyethylene capsules, or may be used directly in multidose powder inhalers.

We claim:

1. An inhalable powder comprising:

(a) an active substance consisting essentially of a compound of formula 1

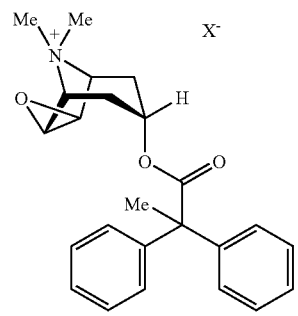

1 wherein $X^-$ is a pharmaceutically acceptable anion; and (b) a physiologically acceptable excipient having an average particle size of 10 μm to 50 μm.

2. The inhalable powder according to claim 1, wherein $X^-$ is chloride, bromide, iodide, sulfate, phosphate, methanesulfonate, nitrate, maleate, acetate, citrate, fumarate, tartrate, oxalate, succinate, benzoate, or p-toluenesulfonate.

3. The inhalable powder according to claim 1, wherein the amount of active substance in the powder based on the pharmacologically active cation of formula 1'

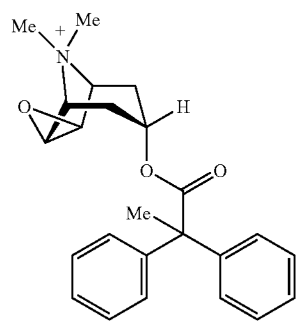

1' is between 0.0008 and 33% by weight.

4. The inhalable powder according to claim 2, wherein the amount of active substance in the powder based on the pharmacologically active cation of formula 1'

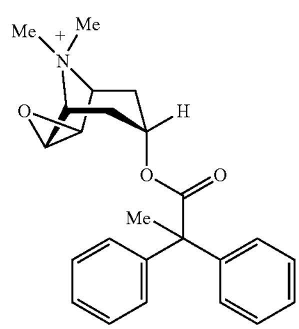

1' is between 0.0008 and 33% by weight.

5. The inhalable powder according to claim 1, wherein the physiologically acceptable excipient is selected from the monosaccharides, disaccharides, oligo- and polysaccharides, polyalcohols, cyclodextrins, amino acids, or the salts thereof.

6. The inhalable powder according to claim 2, wherein the physiologically acceptable excipient is selected from the monosaccharides, disaccharides, oligo- and polysaccharides, polyalcohols, cyclodextrins, amino acids, or the salts thereof.

7. The inhalable powder according to claim 3, wherein the physiologically acceptable excipient is selected from the monosaccharides, disaccharides, oligo- and polysaccharides, polyalcohols, cyclodextrins, amino acids, or the salts thereof.

8. The inhalable powder according to claim 4, wherein the physiologically acceptable excipient is selected from the monosaccharides, disaccharides, oligo- and polysaccharides, polyalcohols, cyclodextrins, amino acids, or the salts thereof.

9. The inhalable powder according to claim 1, wherein the excipient has an average particle size of 12 μm to 35 μm.

10. The inhalable powder according to claim 2, wherein the excipient has an average particle size of 12 μm to 35 μm.

11. The inhalable powder according to claim 3, wherein the excipient has an average particle size of 12 μm to 35 μm.

12. The inhalable powder according to claim 4, wherein the excipient has an average particle size of 12 μm to 35 μm.

13. The inhalable powder according to claim 5, wherein the excipient has an average particle size of 12 μm to 35 μm.

14. The inhalable powder according to claim 1, wherein the excipient has a 10% fine content of 0.5 μm to 6 μm.

15. The inhalable powder according to claim 2, wherein the excipient has a 10% fine content of 0.5 μm to 6 μm.

16. The inhalable powder according to claim 3, wherein the excipient has a 10% fine content of 0.5 μm to 6 μm.

17. The inhalable powder according to claim 4, wherein the excipient has a 10% fine content of 0.5 μm to 6 μm.

18. The inhalable powder according to claim 5, wherein the excipient has a 10% fine content of 0.5 μm to 6 μm.

19. The inhalable powder according to claim 9, wherein the excipient has a 10% fine content of 0.5 μm to 6 μm.

20. The inhalable powder according to claim 1, wherein the excipient has a specific surface area of 0.1 $m^2/g$ to 2 $m^2/g$.

21. The inhalable powder according to claim 2, wherein the excipient has a specific surface area of 0.1 $m^2/g$ to 2 $m^2/g$.

22. The inhalable powder according to claim 3, wherein the excipient has a specific surface area of 0.1 $m^2/g$ to 2 $m^2/g$.

23. The inhalable powder according to claim 4, wherein the excipient has a specific surface area of 0.1 $m^2/g$ to 2 $m^2/g$.

24. The inhalable powder according to claim 5, wherein the excipient has a specific surface area of 0.1 $m^2/g$ to 2 $m^2/g$.

25. The inhalable powder according to claim 9, wherein the excipient has a specific surface area of 0.1 $m^2/g$ to 2 $m^2/g$.

26. The inhalable powder according to claim 19, wherein the excipient has a specific surface area of 0.1 $m^2/g$ to 2 $m^2/g$.

27. A capsule containing the inhalable powder according to one of claims 1, 2, 3, 4, 5, 9, 13, 14, 18, 19, 20, 25, or 26.

28. A capsule according to claim 27, wherein the capsule material comprises synthetic plastics.

29. A kit comprising a capsule according to claim 27, and an inhaler for administering the inhalable powder from the capsule.

30. A kit comprising a capsule according to claim 27, and an Hochrainer-Kinnear inhaler for administering the inhalable powder from the capsule.

* * * * *